(12) United States Patent
Lambert et al.

(10) Patent No.: US 6,999,876 B2
(45) Date of Patent: Feb. 14, 2006

(54) MODULAR ARCHITECTURE FOR RAPID DEPLOYMENT AND COORDINATION OF EMERGENCY EVENT FIELD SURVEILLANCE

(75) Inventors: J. David Lambert, Atlantic Beach, FL (US); John Franklin Alexander, Gainesville, FL (US); Gerald Merckel, Jacksonville, FL (US)

(73) Assignee: University of North Florida, Jacksonville, FL (US)

( * ) Notice: Subject to any disclaimer, the term of this patent is extended or adjusted under 35 U.S.C. 154(b) by 175 days.

(21) Appl. No.: 10/653,312

(22) Filed: Aug. 29, 2003

(65) Prior Publication Data

US 2004/0044553 A1 Mar. 4, 2004

Related U.S. Application Data

(63) Continuation-in-part of application No. 10/409,305, filed on Apr. 8, 2003, now Pat. No. 6,868,340, which is a continuation of application No. 09/822,931, filed on Mar. 30, 2001, now Pat. No. 6,574,561.

(51) Int. Cl.
G06F 19/00 (2006.01)

(52) U.S. Cl. ........................................................ 702/2
(58) Field of Classification Search .................... 702/2, 702/3, 4, 5, 15
See application file for complete search history.

(56) References Cited

U.S. PATENT DOCUMENTS

| | | | |
|---|---|---|---|
| 4,956,875 A | | 9/1990 | Bernard et al. |
| 5,278,539 A | | 1/1994 | Lauterbach et al. |
| 5,555,286 A | * | 9/1996 | Tendler .................... 455/404.2 |
| 5,628,050 A | | 5/1997 | McGraw et al. |
| 5,724,255 A | * | 3/1998 | Smith et al. ................. 700/266 |

(Continued)

OTHER PUBLICATIONS

U.S. Appl. No. 60/271,532.*
U.S. Appl. No. 60/237,984.*
U.S. Appl. No. 60/270,128.*
U.S. Appl. No. 60/221,915.*
U.S. Appl. No. 60/228,051.*
U.S. Appl. No. 60/271,528.*
U.S. Appl. No. 60/271,531.*

*Primary Examiner*—Donald McElheny Jr.
(74) *Attorney, Agent, or Firm*—Thomas C. Saitta

(57) ABSTRACT

A method and system for providing centralized deployment and coordination of field assessment activities. In accordance with one embodiment, an emergency management data processing system includes a field assessment database for storing and processing layered geospatial visual portrayal data and field surveillance attribute data. The emergency management data processing system includes an event setup data input interface for receiving an event identifier associated with an emergency event, a location identifier identifying a portion of the layered geospatial visual portrayal data corresponding to a region affected by the emergency event, and a field surveillance attribute category identifier specifying a category of the stored field surveillance attribute data. The event identifier is then associated with the region data and the specified field surveillance attribute data to generate an event-specific field assessment record.

34 Claims, 5 Drawing Sheets

U.S. PATENT DOCUMENTS

| | | | |
|---|---|---|---|
| 5,815,417 A | | 9/1998 | Orr et al. |
| 5,848,373 A | * | 12/1998 | DeLorme et al. ............ 701/200 |
| 5,867,110 A | * | 2/1999 | Naito et al. ............. 340/286.05 |
| 5,914,675 A | * | 6/1999 | Tognazzini ................. 340/989 |
| 6,002,748 A | | 12/1999 | Leichner |
| 6,023,223 A | * | 2/2000 | Baxter, Jr. .................. 340/531 |
| 6,028,514 A | | 2/2000 | Lemelson et al. |
| 6,084,510 A | | 7/2000 | Lemelson et al. |
| 6,167,255 A | * | 12/2000 | Kennedy et al. .......... 455/414.1 |
| 6,199,045 B1 | * | 3/2001 | Giniger et al. .................. 705/1 |
| 6,273,771 B1 | * | 8/2001 | Buckley et al. ............... 440/84 |
| 6,285,281 B1 | * | 9/2001 | Gatto .................... 340/539.26 |
| 6,360,172 B1 | * | 3/2002 | Burfeind et al. ................ 702/2 |
| 6,429,812 B1 | * | 8/2002 | Hoffberg ................. 342/357.1 |
| 6,542,825 B1 | * | 4/2003 | Jones et al. ..................... 702/3 |
| 6,574,561 B1 | | 6/2003 | Alexander et al. |
| 6,590,529 B1 | * | 7/2003 | Schwoegler ........... 342/357.13 |
| 6,603,405 B1 | * | 8/2003 | Smith ......................... 340/905 |
| 6,771,969 B1 | * | 8/2004 | Chinoy et al. ........... 455/456.1 |
| 2002/0042846 A1 | * | 4/2002 | Bottan et al. ................ 709/249 |
| 2002/0069312 A1 | | 6/2002 | Jones |
| 2002/0188522 A1 | * | 12/2002 | McCall et al. ................ 705/26 |
| 2004/0049345 A1 | * | 3/2004 | McDonough et al. ......... 702/12 |

\* cited by examiner

55

Setup Window 57

EVENT NAME [          ]   TYPE [    ]

SURVEILLANCE LOCATION
- STATE [    ]
- COUNTY [    ]

( GEOGRAPHIC BOUNDARY SELECT )   CITY [    ]

SURVEILLANCE FACILITY/RESOURCE

- Select - ▼
- Hospitals
- Highways
- Fire Stations
- Police Stations
- ⋮

SURVEILLANCE TEAM

FIELD DEVICE 1 [          ]
FIELD DEVICE 2 [          ]
⋮
FIELD DEVICE N [          ]

FIELD REPORT FORMAT

MODULAR ARCHITECTURE FOR RAPID DEPLOYMENT AND COORDINATION OF EMERGENCY EVENT FIELD SURVEILLANCE

CROSS REFERENCE TO RELATED APPLICATIONS

This application is a continuation-in-part of and claims priority from U.S. patent application Ser. No. 10/409,305, entitled "EMERGENCY MANAGEMENT SYSTEM," and filed on Apr. 8, 2003, now U.S. Pat. No. 6,868,340, which is a continuation of Ser. No. 09/822,931 U.S. Pat. No. 6,574,561, entitled "EMERGENCY MANAGEMENT SYSTEM," and filed on Mar. 30, 2001, the contents of which are incorporated herein by reference.

BACKGROUND OF THE INVENTION

1. Technical Field

The present invention relates generally to emergency response management systems, and in particular to an improved data collection and distribution methodology that enables timely responses to rapidly developing and changing environmental conditions.

2. Description of the Related Art

During emergency conditions affecting a particular geopolitical area, it is important that a command and control center, referred to herein as an Emergency Management Center (EMC), receive timely, accurate and comprehensive field assessment information to ensure that available remedial measures and resources are efficiently allocated in a timely and adaptive manner. Such emergency conditions include the aftermath resulting from natural disasters such as hurricanes, tornados, earthquakes or famine, or artificially created disasters resulting from chemical or bio-agent releases, fires, and explosions. The scope of the damage caused by such disasters may be geographically widespread, affecting vast numbers of people and resulting in extensive damage to infrastructure. In the time period immediately following a disaster, an EMC may provide critical assistance in coordinating local civic resources such as police and fire stations, ambulatory services, hospitals, and the like, which may otherwise lack sufficient resources and/or reliable information to enable them to respond efficiently to such geographically dispersed emergency conditions. In addition to coordinating local relief efforts, an EMC also facilitates the allocation of supplemental outside resources that are otherwise subject to misallocation over a widespread area.

An EMC collects field surveillance data from a variety of sources and utilizes this data to render centralized damage assessments required to effectively manage local and outside resource allocation. When disaster conditions are geographically widespread, such as occurs in the aftermath of a hurricane or earthquake, additional, temporary EMCs may be strategically established throughout the affected region resulting in a significant additional level of complexity in establishing the communications and data transfers necessary to effectively coordinate relief efforts. Such conditionally deployed EMCs must quickly establish communications with permanent EMCs operated by local, state and federal agencies tasked to address such disasters.

An exemplary centralized management center is described in U.S. Pat. No. 6,574,561, entitled "EMERGENCY MANAGEMENT SYSTEM," and co-pending U.S. patent application Ser. No. 10/409,305, the contents of which are incorporated herein by reference. The foregoing references describe a system and method for managing the aftermath of a geographically dispersed disaster condition wherein one or more EMCs are established to control multiple, portable field information collection devices utilized by field inspectors to collect damage assessment information. Specifically, the EMCs electronically transmit selected survey forms directing each of the inspectors to collect particular categories of information at specified locations. As each of the individual field inspectors collects and transmits the data back to the EMCs, the data is parsed and combined with maps of the affected geographical region. In this manner, rather than leaving information gathering decisions to the autonomous discretion of the individual inspectors, emergency managers are able to direct inspectors to locations where information is required and to define the type of information to be collected.

Although the foregoing system and method are effective for dynamically assessing field conditions over a specified geographic area in an efficient, centralized manner, there remains a need for providing centralized emergency response deployment and coordination. Conventional computerized emergency management systems utilize technicians to configure the system by selecting and cooperatively deploying several otherwise mutually independent database information categories and programs such as location/map data and emergency response resources such as hospitals and transportation infrastructure. Setting up a centralized emergency assessment response effort is further complicated by situations in which an emergency event, such as a hurricane, is regional in nature encompassing several geopolitical subdivisions, each having their own is localized emergency response systems.

It can therefore be appreciated that a need exists for an improved system and method for providing centralized field assessment coordination and deployment in response to an emergency event. The present invention addresses such a need.

SUMMARY OF THE INVENTION

A method, system and program product that facilitate rapid centralized deployment and coordination of field assessment activities are disclosed herein. In accordance with one embodiment, an emergency management system includes a field assessment database for storing and processing geospatial field map data. The emergency management system further includes an event setup interface for entering and processing an emergency event identifier, a region specifier, and a field surveillance attribute category specifier specifying one or more categories of the stored geospatial field surveillance attribute data. The event setup interface, in cooperation with a geospatial database management system, generates an event-specific field assessment record in which the event identifier is associated with map data corresponding to the specified region, and is further associated with geospatial field surveillance attribute data determined in accordance with the attribute category specifier and the region specifier. In a preferred embodiment, a field assessment team identifier is also entered and processed by the emergency management system to be incorporated into the event-specific field assessment record.

All objects, features, and advantages of the present invention will become apparent in the following detailed written description.

BRIEF DESCRIPTION OF THE DRAWINGS

The novel features believed characteristic of the invention are set forth in the appended claims. The invention itself however, as well as a preferred mode of use, further objects and advantages thereof, will best be understood by reference to the following detailed description of an illustrative embodiment when read in conjunction with the accompanying drawings, wherein:

FIG. 5 depicts an exemplary graphical user interface utilized for specifying the event-specific field assessment record setup data in accordance with the present invention.

DETAILED DESCRIPTION OF A PREFERRED EMBODIMENT

Figure 1:
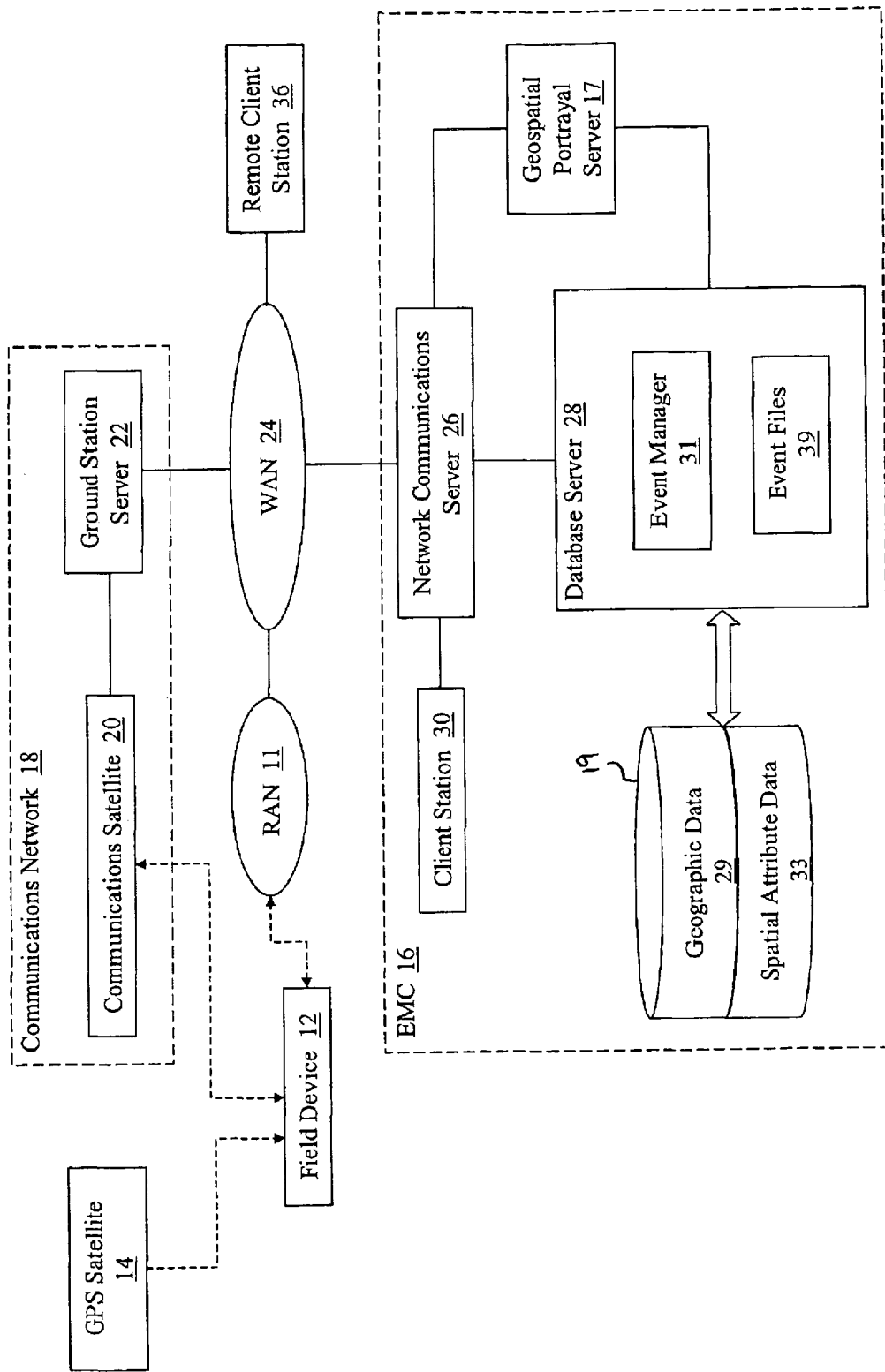
FIG. 1 illustrates an emergency management system for adaptively collecting, processing and communicating field data in response to geographically dispersed emergency event conditions.

The present invention is described in a preferred embodiment in the following description with reference to the figures. While this invention is described in terms of the best mode for achieving this invention's objectives, it will be appreciated by those skilled in the art that variations may be accomplished in view of these teachings without deviating from the spirit or scope of the present invention.

The present invention is directed to a method, system and computer program product for managing field assessment data at a centralized command and control data processing center, referred to herein as an Emergency Management Center (EMC). The invention includes an event manager application having an emergency management setup layer that generates an event-specific field assessment record that associates specified categories of initialization data. The information contained and mutually associated by the generated event-specific field assessment record provides a network accessible and transferable data processing forum for organizing, assigning and tracking field assessment survey efforts.

The event manager application is executed from an EMC data processing system that also includes a field assessment database. In one embodiment, the field assessment database is a geospatial database that stores and processes field map data including multiple categories of field surveillance attribute data that may be overlayed on a graphical map display. The event manager application further includes statistical processing tools for seamlessly generating event-related reports and maps from field report information received from field devices.

The event-specific field assessment records generated by the emergency event setup feature of the present invention enable an EMC to centrally deploy and coordinate field assessment efforts prior to, during, or in the aftermath of an emergency event such as a hurricane, tornado, wildfire, etc. In a preferred embodiment, the emergency event setup feature receives and processes as input into an EMC data processing system a combination of an event identifier in association with data specifiers relating to the geographical region of interest and resident geospatial field surveillance elements. Specifically, an event identifier, typically including a unique alphanumeric name string, is received in association with a region specifier specifying an affected region of interest. The event identifier is further associated with a field surveillance attribute category specifier specifying in individual or categorical terms, an object of field surveillance, such as transportation or medical facilities, to be assessed in current or prospective field survey assessment efforts. In a preferred embodiment, a field device identifier or field surveillance team identifier is incorporated within the event-specific field assessment record, enabling the EMC to utilize the record as a field survey assignment and assignment modification mechanism.

In a preferred embodiment, the event manager application employs, as part of the emergency event setup feature, an event setup page that prompts a user to specify event, region, and surveillance attribute identifiers required to establish an event-specific field assessment record or file. The event setup page is preferably deployed as a graphical user interface (GUI) application, eliminating the need for the user to learn a more complex command-driven interface. The input parameters entered at the event setup page are processed by the EMC to generate one or more event-specific field assessment records that are subsequently utilized to deploy and manage field assessment activities. For example, the data stored and updated in the event-specific field assessment records may be advantageously utilized by the event manager application to generate network-accessible event tracking pages that provide multi-point access to field report information associated with the field assessment records. Each such event tracking page includes graphical display means for displaying the event identifier (a text title or header, for example) in association with the designated geographic region that is overlayed with the geospatial field surveillance attribute data as updated by field report feedback. The event identifier provides an indexing means for identifying and distinguishing between records relating to different events and for identifying sub-events associated with a "parent" event.

The emergency management system of the present invention further includes a local or network accessible field assessment database that stores digitized baseline geospatial data. The baseline geospatial data may include pictorial or iconic representations of spatial elements, such as evacuation facilities, hospitals, emergency response vehicles, and other field observable structures, facilities and systems intended as the object of field assessment surveillance, together with latitude/longitude and possibly altitude geographic position indicators. Associated with the baseline map representation and location data is data relating to the identity and structural or functional assessment characteristics of the object spatial elements. As utilized herein, the term "field surveillance attribute," and close variants thereof, will be utilized to denote the foregoing data types stored and managed by a geospatial database or its equivalent relating to map representation, spatial location, identity, and structural or functional assessment characteristics of spatial elements contained within event-specific field surveillance records.

With reference now to the figures wherein like reference numerals refer to like and corresponding parts throughout, and in particular with reference to FIG. 1, there is depicted an emergency management system 10 that includes a field device 12 equipped with a global positioning system (GPS) receiver (not depicted) for receiving longitude, latitude and altitude information from a set of GPS satellites 14. Field device 12 appends its current GPS position and the date and time at which the position was determined to field assessment reports that are delivered by a satellite communication network 18 or other available network, such as radio area network (RAN) 11, to an emergency management center (EMC) 16 via a Wide Area Network (WAN) 24. Consistent with the intended scope of application of the present invention, WAN 24 may be the Internet or any other computer network that spans a relatively large geographical area and having network connectivity provided by public or private telecommunications infrastructure.

Field assessment surveillance data relating, for example, to infrastructure damage, and the operating status of resource facilities and systems are collected by field device 12, which may be a portable data entry and processing device carried by a field inspector or a mobile intelligent sensor device. Field device 12 combines data processing and network communication functionality including a hardware and software communication interface for establishing a connection with WAN 24 using any combination of communication technologies including satellite, cellular, private radio network, fiber optic etc., over which field assessment information is transmitted to EMC 16. Although only one field device 12 is represented in FIG. 1, emergency management system 10 will typically deploy hundreds or more such field devices dispersed as needed throughout the affected geographical area.

Field device 12 is fundamentally a portable communication device capable of sending field assessment information to EMC 16 and receiving instructions or other information from EMC 16. In one embodiment, field device 12 is a hand-held satellite communications device that incorporates a GPS receiver and portable computing functionality such as the Magellan model GSC 100, available from Magellan Inc. A suitable alternative hand held design for field device 12 is a Personal Digital Assistant (PDA) such as the Palm Pilot manufactured by Palm Pilot, Inc., wherein the device may be modified to include satellite communication interface means. Alternatively, field device 12 may be a cellular telephone having web-enhanced features so that the inspector may link to WAN 24 via a cellular telephone network within RAN 11. In support of its field surveillance report function, field device 12 includes well-known means, such as those employed by various types of PDAs, for acquiring location and time information from the GPS. An integrated GPS receiver (not depicted) enables an inspector to identify the present position of field device 12 and to append this position together with a time mark to field assessment reports that are delivered to EMC 16. In further support of its surveillance information gathering and position ascertainment functions, field device 12 may also include a digital camera, a digital compass, a bar code reader, an RF identification detector, chemical, biohazard and bio-metric detectors, possibly including blood pressure, EKG, finger print recognition, etc.

Field device 12 further includes a display screen enabling the inspector to view visually interactive objects in the form of GUIs and the like, and in particular, to display one or more field assessment forms having an organized hierarchy of defined information entry categories. Although not explicitly depicted herein, the displayed field assessment form preferably includes a menu-driven data input interface enabling an inspector to select and graphically view data contained in event-specific assessment records.

In the depicted embodiment, satellite communication network 18 is a communication satellite network system that includes a ground server station 22 for transmitting messages between one or more communication satellites 20 and WAN 24. The communication satellite system employed by satellite communication network 18 uses low-Earth orbiting satellites instead of terrestrial fixed site relay repeaters to provide worldwide geographic coverage. With this system, two-way alphanumeric packets may be transmitted and received in a manner that is similar to two-way paging or e-mail. The main components of the communication satellite system are a space segment comprising a constellation of low Earth-orbiting satellites 20, and a ground station segment. As will be understood by one familiar with communication satellite networks, the ground station comprises several gateways, including a gateway control center (not shown), a gateway earth station (not shown) and a network control center (not shown). Each ground station further includes at least one server 22 that couples the ground station to WAN 24.

During the initial event surveillance setup phase, and following generation of one or more event-specific field assessment records in the manner set forth hereinbelow, task-specific and location-specific field assessment assignments formulated in accordance with one or more event-specific field assessment records are delivered from EMC 16 to field device 12 over satellite communication network 18 or other presently available communication network such as a terrestrial-based radio area network or the public wired or wireless telephone network. In one embodiment, field assessment data is collected and stored within field device 12 before being downloaded to a field-resident laptop or other portable computer (not depicted) from which the record data is delivered over WAN 24 to EMC 16. During the ensuing field surveillance reporting phase, field device 12 delivers field assessment reports preferably as updates to the original assessment records and optionally receives confirmation of receipt thereof from the available communication network.

In one embodiment, the field assignments are transmitted to field device 12 as primarily text-based instructions directing the field inspector to proceed to a specified location to collect damage assessment information relating to one or more specified field surveillance attribute categories such as, for example, hospitals. The location-specific and task-specific assignment transmitted to field device 12 enables the field inspector to proceed to the specified location and select the field assessment forms or sub-forms into which the collected field assessment data is entered. Such field assignments may be delivered from EMC 16 to field device 12 using well-known e-mail messaging or Short Message Service (SMS) techniques. In the alternative, field assignments may be delivered as a markup language webpage from EMC 16 in response to HyperText Transfer Protocol (HTTP) requests from field device 12.

In one embodiment, field device 12 transmits field assessment report information to EMC 16 as e-mail message attachments. In an alternate embodiment, field device 12 transmits field assessment reports as markup language documents, such as Extensible Markup Language (XML) documents, using HTTP, enabling EMC personnel to view and print the results as well as optionally downloading the source report file. File Transfer Protocol (FTP) can also be utilized for uploading the field reports when the report destination within EMC 16 is a file server. Whether sent via e-mail or as a "pushed" HTTP delivered file, the field assessment report is immediately and automatically integrated into a field assessment database 19.

Communications between WAN 24 and the data processing equipment within EMC 16 are managed by a network communication server 26. Field assessment reports received by network communication server 26 from WAN 24 are delivered to and processed by a database server 28 and a geospatial portrayal server 17 that automatically generate updated graphical status reports and layered geospatial visual portrayals. Database server 28 is essentially a computer system that processes database queries received via network communications server 26. As explained in further detail below, some of the queries processed by database server 28 include requests for information from field assessment database 19, which stores baseline layered geospatial portrayal and field surveillance attribute data. Although not expressly depicted in the figures, it will be appreciated and understood by those skilled in the art that file servers such as database server 28 and geospatial portrayal server 17 necessarily require suitable data processing means such as one of the many commercially available single or multiprocessor designs and data memory and storage means such as read-only memory (ROM), random access memory (RAM), and magnetic and optical disk drives.

The processor and resident operating system utilized by database server 28 and geospatial portrayal server 17 are preferably compatible with commercially available software developed by Environmental Systems Research Institute, Inc. (ESRI®) known as Spatial Database. Engine (SDE®) which is a client/server application enabling geographic data to be stored, managed, and quickly retrieved from leading commercial database management systems such as Oracle®, Microsoft SQL Server, Sybase®, IBM DB2®, and Informix®.

In association with database server 28, field assessment database 19 maintains a collection of baseline emergency response support data. Specifically, field assessment database 19 includes baseline layered geospatial visual portrayal and field surveillance attribute data. Sources of such layered geospatial visual portrayal data include geographic information system (GIS) map data or other digitized map data. The field surveillance attribute data includes data describing and/or identifying any person, resource, structure, device or system that is observable by a field inspector as an object of field assessment efforts. A field surveillance attribute may include structural facilities such as hospitals, police stations, transportation structures such as roads and highways, vehicles, etc.

In one embodiment, field assessment database 19 stores geospatial data comprising geographic data 29 and spatial attribute data 33. Geographic data 29 may include, for example, location data comprising latitude, longitude and altitude, as well as street addresses, city, state, etc. Spatial attribute data 33 comprises data that may be selectively retrieved by event setup application 35 in accordance with the specified field surveillance attribute category, representing geographic elements including buildings, bridges, streets, highways and other geographically specific entities. Field assessment database 19 is maintained on a disk drive storage device (not depicted), which may be any commercially available storage device suitable for a large capacity server application such as a Redundant Array of Independent Disks (RAID) storage system. The disk drive storage device may be augmented by distributed data storage, such as storage networks supported by the IP-based Internet Small Computer System Interface (iSCSI) standard, and accessible by the resident server processor via a network connection.

Database server 28 accesses baseline geospatial data from field assessment database 19 and processes this data in accordance with field report feedback data from field inspectors to generate detailed reports and layered geospatial visual portrayals using specialized software applications such as ArcGIS, and ArcGIS Internet Map Server (IMS) software. Database server 28 stores the field assessment report data locally, buffering and passing back to a requesting client only the data that meets the client's search criteria. The reports and layered geospatial visual portrayals generated by database server 28 in concert with geospatial portrayal server 17 may be delivered to or browser-retrieved by client 36, which may be any networked device such as a printer, plotter or a computer system capable of accessing database server 28 to generate statistical and graphical information of interest to emergency managers.

Figure 4:
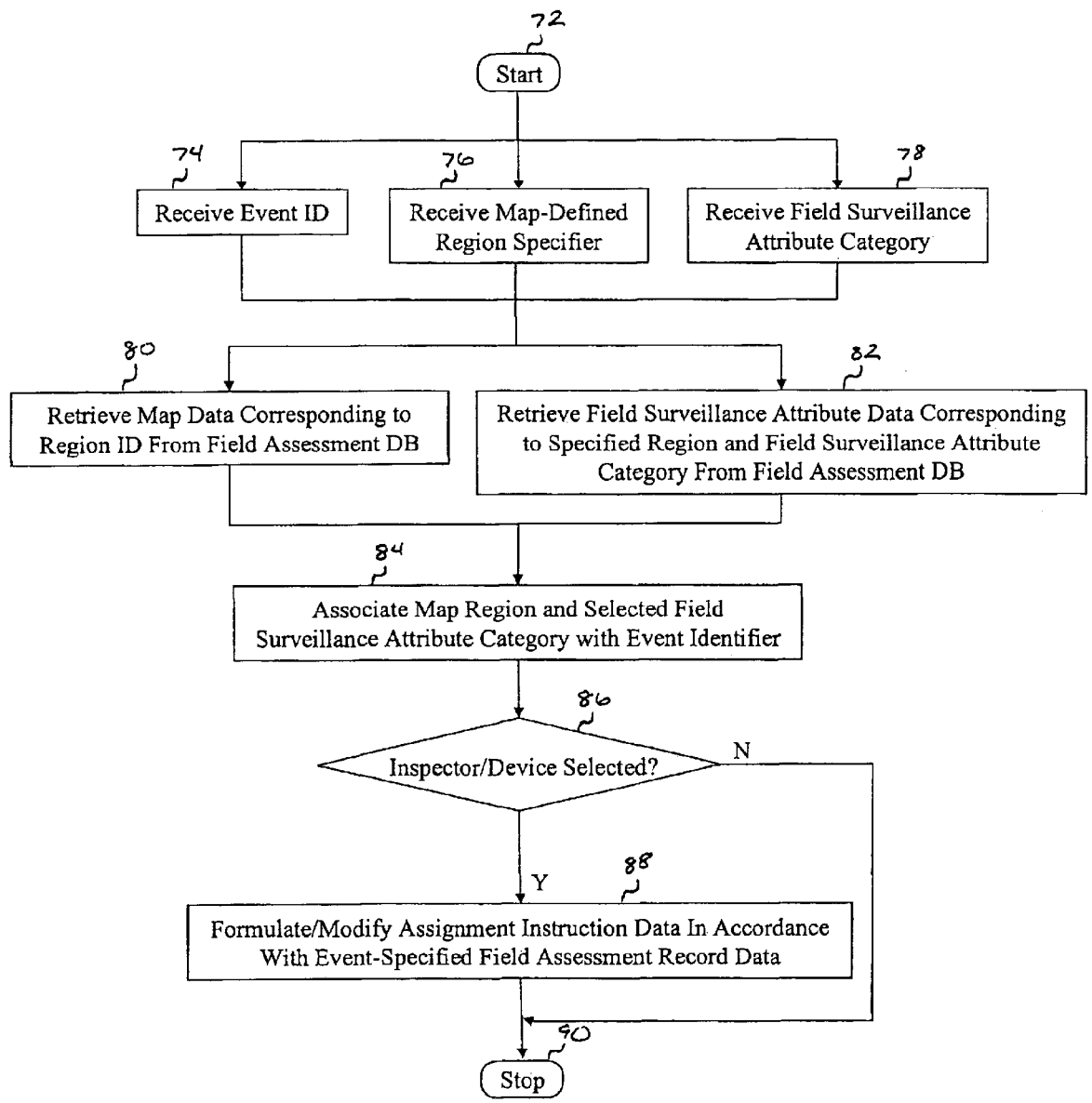
FIG. 4 is a flow diagram illustrating a database server-side process for generating an event-specific field assessment record in accordance with the present invention.

As further depicted in FIG. 1, an event manager application 31 is included in the suite of database management facilities employed by database server 28. As explained in further detail below with reference to FIGS. 2 and 4, event manager 31 includes data management, retrieval, and processing instructions for the surveillance assignment and field report processing phases of emergency management. A set of one or more event-specific field assessment records and/or event files 39, described in further detail with reference to FIGS. 2 and 4, are generated by the processing of specified event setup parameters by event manager 31.

Figure 2:
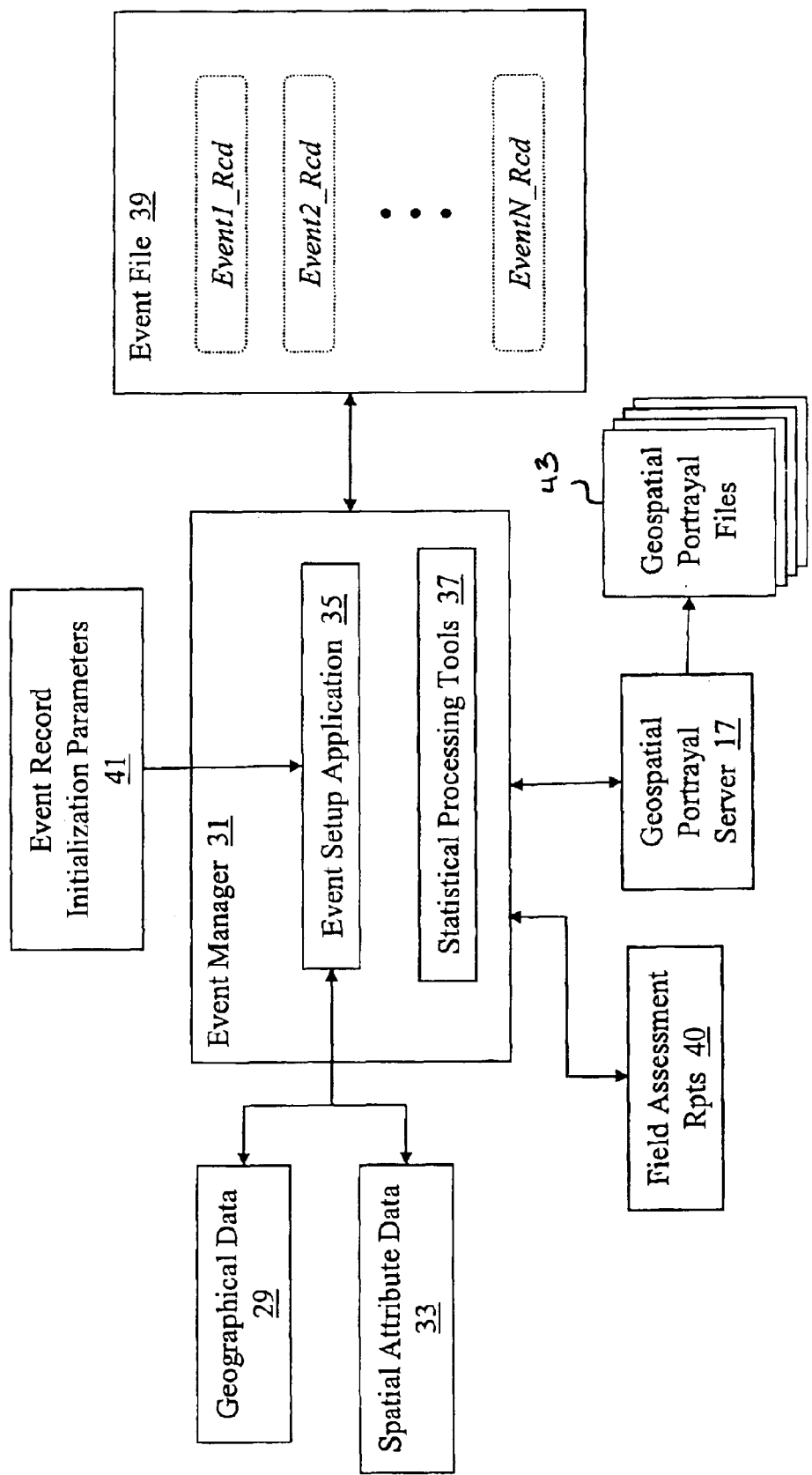
FIG. 2 is a block diagram representation of the data structures and program modules utilized by the emergency management system in accordance with the present invention.

With reference to FIG. 2, there is depicted a block diagram representation of data structures and program modules, including event manager 31, utilized by EMS 10 to provide centralized deployment and coordination of field assessment activities. As shown in FIG. 2, event manager 31 includes an event setup application 35 and statistical processing tools 37. In accordance with the present invention, event setup application 35 generates event-specific field assessment records, such as Event1_Rcd through EventN_Rcd, possibly incorporated within an event file 39, and which are stored, distributed, updated and modified by EMC 16 in support of field assessment activities. In general, each of the event-specific records includes a unique event identifier associated with specified region and field surveillance attribute data. The event-specific records are preferably organized and maintained in accordance with database techniques wherein each record is uniquely identifiable and retrievable locally within EMC 16 or remotely by client 36. The manner in which the event-specific field assessment records are maintained by event manager 31 depends on the type of database management system from which event manager 31 is deployed. For example, if event manager 31 is deployed from or as part of a relational database management system, the event-specific field assessment records will be maintained in the table-structured manner characteristic of relational databases. Other possible approaches for database setup and management include software applications characterized by ASP or NET.

Event manager 31 further includes a set of statistical processing tools 37 that retrieve and process the event-specific records within event file 39 to generate output reports (not depicted) that may include displayable or printable data files utilized by EMC 16 for event tracking purposes. Although not depicted in detail herein, event manager 31 further includes program and instruction means for defining the nature, content, format and style of reports desired by EMC personnel.

The data to be included within event-specific records Event1_Rcd through EventN_Rcd is retrieved from geographic data 29 and spatial attribute data 33 within field assessment database 19 corresponding to a set of initialization parameters 41 as explained in further detail with reference to FIGS. 3 and 4. Event-specific records Event1_Rcd through EventN_Rcd are locally stored and individually retrievable from database server 28 and may be utilized to formulate field surveillance assignments that are transmitted to one or more field devices. In a preferred embodiment, field report feedback, received as field assessment reports 40 from field devices in association with an event-specific record formulated field surveillance assigments, may be utilized to update or modify the original record.

Figure 3:
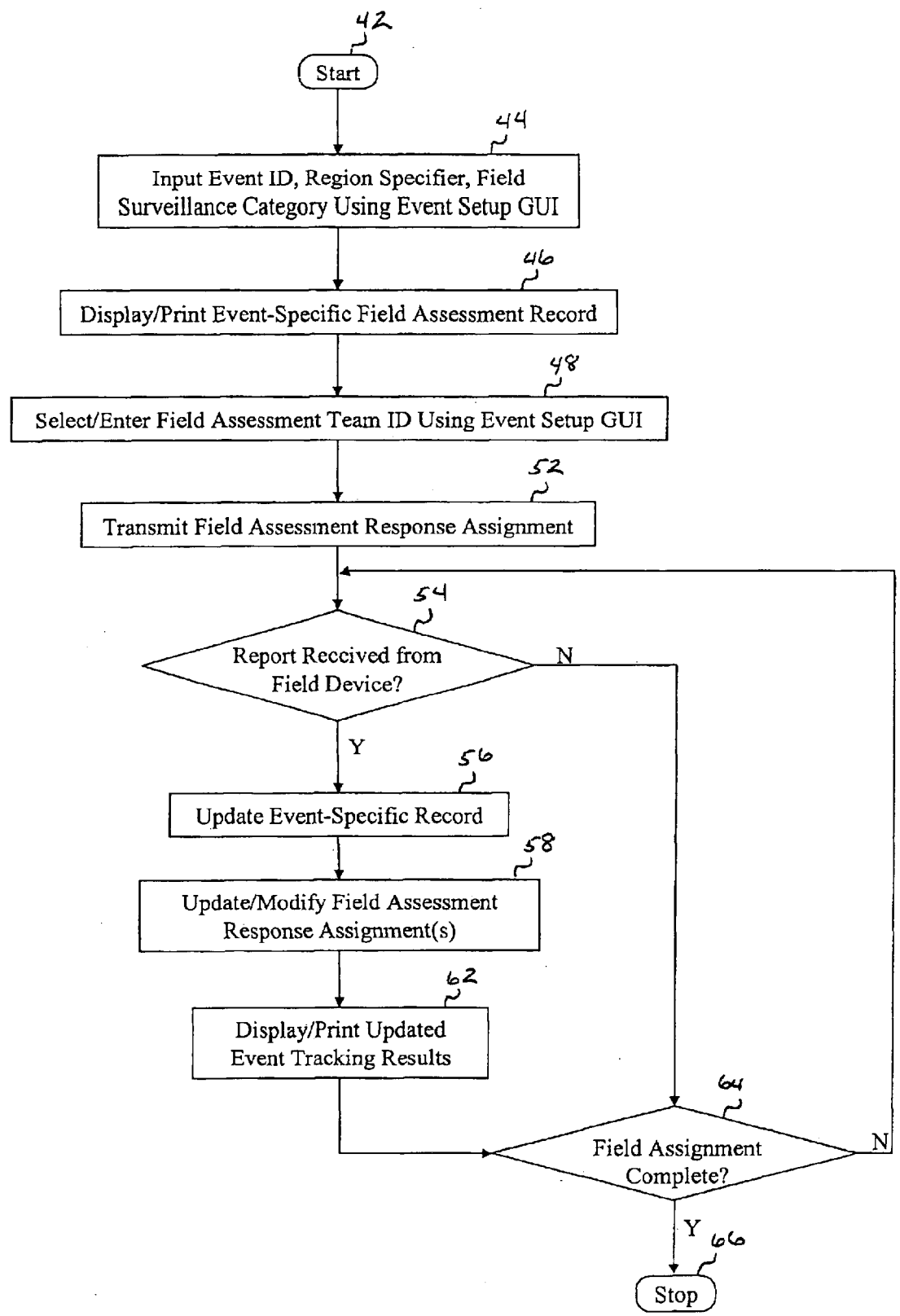
FIG. 3 is a flow diagram depicting a client-side process for generating and utilizing an event-specific field assessment record in accordance with the present invention.

With reference to FIG. 3, there is depicted a flow diagram illustrating client-side method steps for generating and utilizing an event-specific field assessment record in accordance with a preferred embodiment of the present invention. The process begins as shown at steps 42 and 44 with a local or remote client-side user inputting an event identifier, a region specifier, and a field surveillance attribute category as prompted by selectable menu items or data entry fields of an event setup GUI such as that depicted in FIG. 5. The event identifier preferably includes an alphanumeric text string denoting an event name and optionally includes an event type specifier selected from a drop-down list provided on the event setup GUI such as that illustrated in FIG. 5. The location identifier may be specified in terms of geo-political or geographical boundaries, or in the alternate may be designated using GUI means, such as cursor manipulation over a representative layered geospatial visual portrayal image displayed, for example, on a computer monitor. The field surveillance attribute categories, which in one embodiment correspond to geospatial field category layers, are preferably selected using GUI means such as a drop-down list from a list of field attribute categories. The event identifier, region specifier and field surveillance attribute categories are preferably entered as independently selectable data input parameters into an event setup GUI that may comprise one or more data input windows.

The process continues as depicted at step 46 with the display of an event-specific field assessment record or file generated by event setup application 35 in accordance with the parameters input at step 44. The server-side process for generating the event-specific record is illustrated in further detail with reference to FIG. 4. Continuing with the client-side process, and as illustrated at step 48, the user selects from a selectable GUI list or menu object or enters into a text field, the identity of one or more field inspectors and/or field devices, such as field device 12. In one embodiment, the inspectors/devices are assigned individually as a defacto field surveillance "team" with the electronically stored association maintained on an individual basis while in an alternate embodiment, the inspectors/devices are assigned as a group having a group identifier.

Next, as depicted at step 52, the local or remote client transmits a field surveillance assignment from EMC 16 to the one or more field devices specified either directly or by field inspector identity at step 48. The field surveillance assignment is preferably formulated in accordance with one or more event-specific field assessment records as characterized herein. EMC 16 awaits feedback reports corresponding to each of the field surveillance assignments as illustrated at step 54. Responsive to receiving a field assessment report having an event identifier corresponding to the event identifier of a transmitted field surveillance assignment, event manager 31 updates the corresponding event-specific field assessment record within database server 28 as shown at step 56. Record update step 56 may include modifying a damage status description of the resource identified by the associated field surveillance attribute. For example, if a the field surveillance attribute specified at step 44 was for "hospital," or specified a particular hospital, and the received field assessment report indicated that electrical power to the specified hospital(s) is observed by the inspector/intelligent sensor to have been interrupted, the event-specific record would be updated to reflect the interrupted power supply at the hospital(s). Additionally, and as depicted at step 58, the field assessment assignment for the reporting inspector/field device may be modified in accordance with the update content of the received field assessment report. Using the foregoing example of a reported power interruption at a hospital, event manager 31 may modify the original field surveillance assignment in accordance with the field assessment record update to include "power supply," for example, as an additional field surveillance attribute to be assessed within the specified location. As illustrated at step 62, the results of the updated field assessment record may be displayed and printed at local or remote client side stations. As depicted at steps 54 and 64, the foregoing process continues until the field assessments assignments are completed and the process ends as shown at step 66.

FIG. 5 illustrates an event setup GUI 55 in accordance with one embodiment of the present invention. As shown in FIG. 5, event setup GUI 55 is contained within the active operating environment of a setup window 57 containing several selectable icon and data entry field objects. In a preferred embodiment, a pointing device (not depicted) is used to select/activate the various objects and data entry fields including those displayed under EVENT NAME, SURVEILLANCE LOCATION and SURVEILLANCE TEAM. Among the selectable icons is a geographical boundary select button that launches a geographical zoom/ select application enabling the user to specify the desired surveillance region location directly on a displayed layered geospatial visual portrayal using selectable/adjustable boundaries. Field surveillance resource attribute(s) are selected within event setup GUI 55 by selecting menu-listed surveillance facilities denoted in categorical terms such as hospitals, highways, fire stations, police stations, etc. Similarly, inspection team identifiers and requested field report format specifiers are provided as user-selectable data entry fields within event setup GUI 55.

Referring to FIG. 4, there is illustrated a flow diagram illustrating a database server-side process for generating an event-specific field assessment record in accordance with the present invention. The process begins as shown at step 72 and proceeds to steps 74, 76 and 78 depicting receipt by event setup application 35 of the input parameters specified at step 44 in FIG. 3. An event identifier is received (step 74) which is utilized both by event manager 31 (possibly in accordance with the relational database management application from which event manager 31 is deployed) as well as by persons viewing the object record, as the unique record identifier. A region specifier and a field surveillance attribute category specifier are also received by event setup application 35 (steps 76 and 78) in association with the event identifier. In one embodiment, the event, location and field surveillance attribute identifiers may be received responsive to user input into event setup GUI 55 (see FIG. 5) which preferably serves as the input program interface for event manager 31.

Next, as illustrated at step 80, event setup application 35 retrieves layered geospatial visual portrayal data corresponding to the received region specifier from the geographic data 29 maintained by field assessment database 19. For example, if the region specifier specifies Duval County, Florida, event setup application 35 retrieves data from geographic data 29 that may be utilized to generate a screen and/or print displayable representation of the geographical and/or geo-political boundaries of the same. Furthermore, as depicted at step 82, event setup application 35 retrieves field surveillance attribute data corresponding to the received field surveillance attribute specifier from field assessment database 19. The received field surveillance attribute identifier may be expressed as a categorical identifier, such as "hospitals," or in the alternative, as an individually specific identifier, such as "Duval County Hospital." In the former case, the field surveillance attribute data retrieved by event setup application 35 will correspond to both the region specified by the region specifier and the categorical field surveillance attribute specifier. In this manner, and continuing with the foregoing examples, a designation of "hospitals" as the field surveillance attribute category, received in association with a location identifier specifying "Duval Country, Florida," prompts event setup application 35 to retrieve data from field assessment database 19 describing and/or identifying all hospitals located within said county. If instead, an individually specific field surveillance attribute identifier such as "Duval Country Hospital" is used, event setup application 35 retrieves data from field assessment database 19 describing and/or identifying said particular hospital.

Following retrieval of the layered geospatial visual portrayal and field surveillance attribute data, and as depicted at step 84, event setup application 35 associates the respective layered geospatial visual portrayal and field surveillance attribute data retrieved from field assessment database 19 with the unique event identifier entered in association therewith. In accordance with a preferred embodiment, the association of the event identifier with the retrieved location and field surveillance attribute data is accomplished by the generation of an event-specific record, such as the event-specific records depicted in FIG. 2, utilizing table indexing or other such database record and file organizational techniques.

Proceeding to step 86, if the identities of one or more field inspectors and/or field devices have been specified in association with a field inspection team as depicted at step 48 of FIG. 3, a field surveillance assignment is formulated in accordance with the event-specific record information as depicted at step 88. The location of the assignment is determined in accordance with the region specified by the location identifier and the surveillance "task," in terms of the structures, facilities or resources that are to be observed and reported upon, are determined in accordance with the data retrieved in accordance with the received field surveillance attribute identifier. In a preferred embodiment, the field surveillance assignment step further includes the step of transmitting a response assignment instruction that instructs the recipient field device to display a field assessment form that specifies the assigned location and prompts the inspector for input data relating to the field surveillance attribute specified by the assignment. If an inspection team parameter is not received the process ends as shown at steps 86 and 90.

Preferred implementations of the invention include implementations as a computer system programmed to execute the method or methods described herein, and as a program product. According to the computer system implementation, sets of instructions for executing the method and system of the present invention are resident in a storage device such as the read-only memory (ROM) or random access memory (RAM) of one or more computer systems. Until required by the computer system, the set of instructions may be stored as a computer-program product in another computer data storage device such as a disk drive that may include a removable storage media such as an optical disk or floppy disk for eventual utilization in the disk drive.

While this invention has been described in terms of several embodiments, it is contemplated that alterations, permutations, and equivalents thereof will become apparent to one of ordinary skill in the art upon reading this specification in view of the drawings supplied herewith. It is therefore intended that the invention and any claims related thereto include all such alterations, permutations, and equivalents that are encompassed by the spirit and scope of this invention.

What is claimed is:

1. A method for deploying and coordinating field assessment surveillance in response to an emergency event, said method comprising:
   receiving as mutually associated input to an emergency management data processing system:
      an event identifier;
      a region specifier; and
      a field surveillance attribute category specifier; and
   generating an event-specific field assessment record that associates the event identifier with the specified region and the specified field surveillance attribute category;
   wherein the emergency management data processing system includes a field assessment database for storing and processing field surveillance attribute data, and wherein said generating an event-specific field assessment record comprises retrieving field surveillance attribute data from the field assessment database corresponding to the geographic area specified by the region specifier and further corresponding to the specified field surveillance attribute category; and
   wherein said generating an event-specific field assessment record comprises associating a set of one or more mobile data collection entities with the event identifier, the specified region and the specified field surveillance attribute category;
   wherein the event-specific field assessment record is a geospatial data record stored in a geospatial database that indexes the event-specific field assessment record in accordance with the event identifier; and
   deploying and coordinating field assessment surveillance responsive to said input and said event-specific field assessment record.

2. The method of claim 1, wherein the event identifier includes an event name.

3. The method of claim 2, wherein the event identifier further includes an event category.

4. The method of claim 1, wherein the region specifier specifies a geographic area.

5. The method of claim 1, wherein the field surveillance attribute category specifier specifies an emergency response resource category.

6. The method of claim 5, wherein the field surveillance attribute category specifier specifies a field surveillance attribute category included among the group comprising transportation facilities, communications facilities, health care facilities, persons, households, and law enforcement facilities.

7. The method of claim 1, wherein the field assessment database is a geospatial database.

8. The method of claim 1, further comprising generating an event tracking display that displays the event identifier in association with layered geospatial visual portrayal data corresponding to the specified region and the specified field surveillance attribute category.

9. The method of claim 8, wherein said generating an event tracking display comprises generating the event tracking display on a computer display output device.

10. The method of claim 8, wherein said generating an event tracking display comprises generating the event tracking display on a printed output medium.

11. The method of claim 8, wherein said generating an event tracking display comprises overlaying the layered geospatial visual portrayal data corresponding to the specified field surveillance attribute category on the displayed region.

12. The method of claim 1, wherein said associating a set of one or more mobile data collection entities with the event identifier, the specified region and the specified field surveillance attribute category further includes associating a field assessment team identifier that identifies a set of one or more field inspectors to be assigned a field assessment task.

13. The method of claim 1, wherein said associating a set of one or more mobile data collection entities with the event identifier, the specified region and the specified field surveillance attribute category further includes receiving as input to the emergency management data processing system a field assessment team identifier that identifies a set of one or more mobile field devices to be assigned a field assessment task.

14. The method of claim 13, further comprising delivering a task-specific and location-specific field surveillance instruction to at least one of the one or more of the identified mobile field devices.

15. The method of claim 14, wherein said delivering a task-specific and location-specific field surveillance instruction comprises electronically transmitting an assignment instruction instructing the one or more mobile field devices to display a field assessment form that specifies an assigned location and prompts a user for input data relating to a field surveillance attribute, wherein the assigned location and field surveillance attribute are determined in accordance with the generated event-specific field assessment record.

16. A computer program product for deploying and coordinating field assessment surveillance in response to an emergency event, said program product comprising:
instruction means for receiving as mutually associated input to an emergency management data processing system:
an event identifier;
a region specifier; and
a field surveillance attribute category specifier; and
instruction means for generating an event-specific field assessment record that associates the event identifier with the specified region and the specified field surveillance attribute category;
wherein the emergency management data processing system includes a field assessment database for storing and processing field surveillance attribute data, and wherein said instruction means for generating an event-specific field assessment record comprises instruction means for retrieving field surveillance attribute data from the field assessment database corresponding to the geographic area specified by the region specifier and further corresponding to the specified field surveillance attribute category; and
wherein the event-specific field assessment record is a geospatial data record stored in a geospatial database that indexes the event-specific field assessment record in accordance with the event identifier.

17. The program product of claim 16, wherein the event identifier includes an event name.

18. The program product of claim 17, wherein the event identifier further includes an event category.

19. The program product of claim 16, wherein the region specifier specifies a geographic area.

20. The program product of claim 16, wherein the field surveillance attribute category specifier specifies an emergency response resource category.

21. The program product of claim 20, wherein the field surveillance attribute category specifier specifies a field surveillance attribute category included among the group comprising transportation facilities, communications facilities, health care facilities, persons, households, and law enforcement facilities.

22. The program product of claim 16, wherein the field assessment database is a geospatial database.

23. The program product of claim 16, further comprising instruction means for generating an event tracking display that displays the event identifier in association with layered geospatial visual portrayal data corresponding to the specified region and the specified field surveillance attribute category.

24. The program product of claim 23, wherein said instruction means for generating an event tracking display comprises instruction means for generating the event tracking display on a computer display output device.

25. The program product of claim 23, wherein said instruction means for generating an event tracking display comprises instruction means for generating the event tracking display on a printed output medium.

26. The program product of claim 23, wherein said instruction means for generating an event tracking display comprises instruction means for overlaying the layered geospatial visual portrayal data corresponding to the specified field surveillance attribute category on the displayed region.

27. The program product of claim 16, wherein said instruction means for generating an event-specific field assessment record comprises instruction means for associating a set of one or more mobile data collection entities with the event identifier, the specified region and the specified field surveillance attribute category.

28. The program product of claim 27, wherein said instruction means for associating a set of one or more mobile data collection entities with the event identifier, the specified region and the specified field surveillance attribute category further includes instruction means for associating a field assessment team identifier that identifies a set of one or more field inspectors to be assigned a field assessment task.

29. The program product of claim 27, wherein said instruction means for associating a set of one or more mobile data collection entities with the event identifier, the specified region and the specified field surveillance attribute category further includes instruction means for receiving as input to the emergency management data processing system a field assessment team identifier that identifies a set of one or more mobile field devices to be assigned a field assessment task.

30. The program product of claim 29, further comprising instruction means for delivering a task-specific and location-specific field surveillance instruction to at least one of the one or more of the identified mobile field devices.

31. The program product of claim 30, wherein said instruction means for delivering a task-specific and location-specific field surveillance instruction comprises instruction means for instructing the one or more mobile field devices to display a field assessment form that specifies an assigned location and prompts a user for input data relating to a field surveillance attribute, wherein the assigned location and field surveillance attribute are determined in accordance with the generated event-specific field assessment record.

32. A method for deploying and coordinating field assessment surveillance in response to an emergency event, said method comprising:
- receiving as input parameters to a geospatial database management system:
  - an event identifier;
  - a region specifier; and
  - at least one field surveillance attribute category; and
- responsive to said receiving step, generating an event-specific field assessment record that associates the event identifier with the specified region and the at least one field surveillance category;
- wherein the event identifier, the region specifier and the at least one field surveillance attribute category are received from a local or remote client data processing system, said method further comprising entering the event identifier, the region specifier and the at least one field surveillance attribute category as user input entries on an event setup graphical user interface on the local or remote client data processing system; and
- wherein said generating an event-specific field assessment record includes retrieving from a field assessment database field surveillance attribute data corresponding to the specified field surveillance attribute category and the specified region.

33. The method of claim 32, wherein the field assessment database is a geospatial database that associates spatial coordinates with the field surveillance attribute data.

34. The method of claim 32, further comprising generating an emergency event tracking display that displays a layered geospatial visual portrayal representation of the specified region and the at least one field surveillance attribute in association with the event identifier.

* * * * *